US009125717B2

(12) United States Patent
Alexander

(10) Patent No.: US 9,125,717 B2
(45) Date of Patent: Sep. 8, 2015

(54) IMPLANT TENSION ADJUSTMENT SYSTEM AND METHOD

(75) Inventor: James A. Alexander, Excelsior, MN (US)

(73) Assignee: AMS Research Corporation, Minnetonka, MN (US)

(*) Notice: Subject to any disclaimer, the term of this patent is extended or adjusted under 35 U.S.C. 154(b) by 131 days.

(21) Appl. No.: 13/229,460

(22) Filed: Sep. 9, 2011

(65) Prior Publication Data

US 2012/0215058 A1   Aug. 23, 2012

Related U.S. Application Data

(60) Provisional application No. 61/445,840, filed on Feb. 23, 2011.

(51) Int. Cl.
*A61F 2/02* (2006.01)
*A61F 2/00* (2006.01)

(52) U.S. Cl.
CPC ....... *A61F 2/0045* (2013.01); *A61F 2250/0003* (2013.01); *A61F 2250/0012* (2013.01)

(58) Field of Classification Search
USPC .............. 600/29–32, 37; 606/151–153, 157
See application file for complete search history.

(56) References Cited

U.S. PATENT DOCUMENTS

| | | |
|---|---|---|
| 3,384,073 A | 5/1968 | Van Winkle, Jr. |
| 3,789,828 A | 2/1974 | Schulte |
| 4,548,202 A | 10/1985 | Duncan |
| 4,632,100 A | 12/1986 | Somers et al. |
| 4,873,976 A | 10/1989 | Schreiber |
| 4,938,760 A | 7/1990 | Burton et al. |
| 4,969,892 A | 11/1990 | Burton et al. |
| 4,979,956 A | 12/1990 | Silvestrini |
| 5,013,292 A | 5/1991 | Lemay |
| 5,013,316 A | 5/1991 | Goble et al. |
| 5,019,032 A | 5/1991 | Robertson |
| 5,053,043 A | 10/1991 | Gottesman et al. |
| 5,085,661 A | 2/1992 | Moss |
| 5,112,344 A | 5/1992 | Petros |
| 5,141,520 A | 8/1992 | Goble et al. |
| 5,149,329 A | 9/1992 | Richardson |
| 5,188,636 A | 2/1993 | Fedotov |

(Continued)

FOREIGN PATENT DOCUMENTS

| | | |
|---|---|---|
| AU | 2002241673 | 11/2005 |
| CA | 2404459 | 8/2005 |

(Continued)

OTHER PUBLICATIONS

"Anchor" Merriam-Webster.com. http://www.merriam-webster.com/dictionary/anchor. May 8, 2011.*

(Continued)

*Primary Examiner* — Samuel Gilbert
(74) *Attorney, Agent, or Firm* — Skaar Ulbrich Macari, P.A.

(57) ABSTRACT

An implant or sling device is provided with a tension adjustment system. The adjustment system can include one or more small pressure bulbs placed against the inferior pubic rami for support. By palpating the bulbs (one on left and one on right), the pressure can be adjusted to control the tension of the implant. Other conduits, balloons, introduction tools, ports and fluid adjustment components and mechanisms can be included to provide selective adjustment of the tension of the implant relative to the supported tissue or organ.

15 Claims, 5 Drawing Sheets

(56) References Cited

U.S. PATENT DOCUMENTS

| | | |
|---|---|---|
| 5,203,864 A | 4/1993 | Phillips |
| 5,209,756 A | 5/1993 | Seedhom et al. |
| 5,256,133 A | 10/1993 | Spitz |
| 5,268,001 A | 12/1993 | Nicholson et al. |
| 5,269,783 A | 12/1993 | Sander |
| 5,328,077 A | 7/1994 | Lou |
| 5,337,736 A | 8/1994 | Reddy |
| 5,354,292 A | 10/1994 | Braeuer et al. |
| 5,362,294 A | 11/1994 | Seitzinger |
| 5,370,662 A | 12/1994 | Stone et al. |
| 5,376,097 A | 12/1994 | Phillips |
| 5,383,904 A | 1/1995 | Totakura et al. |
| 5,520,700 A | 5/1996 | Beyar et al. |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,584,860 A | 12/1996 | Goble et al. |
| 5,591,163 A | 1/1997 | Thompson |
| 5,591,206 A | 1/1997 | Moufarrege |
| 5,628,756 A | 5/1997 | Barker, Jr. et al. |
| 5,643,320 A | 7/1997 | Lower et al. |
| 5,647,836 A | 7/1997 | Blake et al. |
| 5,669,935 A | 9/1997 | Rosenman et al. |
| 5,674,247 A | 10/1997 | Sohn |
| 5,690,655 A | 11/1997 | Hart et al. |
| 5,697,931 A | 12/1997 | Thompson |
| 5,709,708 A | 1/1998 | Thal |
| 5,725,529 A | 3/1998 | Nicholson et al. |
| 5,725,541 A | 3/1998 | Anspach, III et al. |
| 5,741,282 A | 4/1998 | Anspach, III et al. |
| 5,782,862 A | 7/1998 | Bonuttie |
| 5,807,403 A | 9/1998 | Beyar et al. |
| 5,836,314 A | 11/1998 | Benderev et al. |
| 5,842,478 A | 12/1998 | Benderev et al. |
| 5,873,891 A | 2/1999 | Sohn |
| 5,899,909 A | 5/1999 | Claren et al. |
| 5,904,692 A | 5/1999 | Steckel et al. |
| 5,922,026 A | 7/1999 | Chin |
| 5,925,047 A | 7/1999 | Errico et al. |
| 5,934,283 A | 8/1999 | Willem et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,007,539 A | 12/1999 | Kirsch et al. |
| 6,010,447 A | 1/2000 | Kardjian |
| 6,019,768 A | 2/2000 | Wenstrom et al. |
| 6,027,523 A | 2/2000 | Schmieding |
| 6,036,701 A | 3/2000 | Rosenman |
| 6,039,686 A * | 3/2000 | Kovac .................. 600/30 |
| 6,042,534 A | 3/2000 | Gellman et al. |
| 6,042,536 A | 3/2000 | Tihon et al. |
| 6,048,351 A | 4/2000 | Gordon et al. |
| 6,053,935 A | 4/2000 | Brenneman et al. |
| 6,056,688 A | 5/2000 | Benderev et al. |
| 6,068,591 A | 5/2000 | Bruckner et al. |
| 6,077,216 A | 6/2000 | Benderev et al. |
| 6,099,551 A | 8/2000 | Gabby |
| 6,099,552 A | 8/2000 | Adams |
| 6,106,545 A | 8/2000 | Egan |
| 6,110,101 A | 8/2000 | Tihon et al. |
| 6,117,067 A * | 9/2000 | Gil-Vernet .................. 600/30 |
| 6,127,597 A | 10/2000 | Beyar et al. |
| 6,168,611 B1 | 1/2001 | Risvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,306,079 B1 | 10/2001 | Trabucco |
| 6,319,272 B1 | 11/2001 | Brenneman |
| 6,322,492 B1 | 11/2001 | Kovac |
| 6,328,686 B1 | 12/2001 | Kovac |
| 6,334,446 B1 | 1/2002 | Beyar |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,423,072 B1 | 7/2002 | Zappala |
| 6,423,080 B1 | 7/2002 | Gellman et al. |
| 6,440,154 B2 | 8/2002 | Gellman et al. |
| 6,451,024 B1 | 9/2002 | Thompson et al. |
| 6,454,778 B2 | 9/2002 | Kortenbach |
| 6,475,139 B1 | 11/2002 | Miller |
| 6,478,727 B2 | 11/2002 | Scetbon |
| 6,491,703 B1 | 12/2002 | Ulmsten |
| 6,506,190 B1 | 1/2003 | Walshe |
| 6,544,273 B1 | 4/2003 | Harari et al. |
| 6,575,897 B1 | 6/2003 | Ory |
| 6,582,443 B2 | 6/2003 | Cabak et al. |
| 6,592,610 B2 | 7/2003 | Beyar |
| 6,599,235 B2 | 7/2003 | Kovac |
| 6,612,977 B2 | 9/2003 | Staskin |
| 6,635,058 B2 | 10/2003 | Beyar et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,702,827 B1 | 3/2004 | Lund |
| 6,730,110 B1 | 5/2004 | Harari et al. |
| 6,746,455 B2 | 6/2004 | Beyar et al. |
| 6,755,781 B2 | 6/2004 | Gellman |
| 6,881,184 B2 | 4/2005 | Zappala |
| 6,908,425 B2 | 6/2005 | Luscombe |
| 6,908,473 B2 | 6/2005 | Skiba et al. |
| 6,911,002 B2 | 6/2005 | Fierro |
| 6,953,428 B2 | 10/2005 | Gellman et al. |
| 6,960,160 B2 | 11/2005 | Browning |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,025,063 B2 | 4/2006 | Snitkin |
| 7,025,772 B2 | 4/2006 | Gellman et al. |
| 7,048,682 B2 | 5/2006 | Neisz et al. |
| 7,056,333 B2 | 6/2006 | Walshe |
| 7,070,558 B2 | 7/2006 | Gellman et al. |
| 7,083,568 B2 | 8/2006 | Neisz et al. |
| 7,087,065 B2 | 8/2006 | Ulmsten et al. |
| 7,112,171 B2 | 9/2006 | Rocheleau et al. |
| 7,112,210 B2 | 9/2006 | Ulmsten et al. |
| 7,121,997 B2 | 10/2006 | Kammerer et al. |
| 7,198,597 B2 | 4/2007 | Siegel et al. |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,267,645 B2 | 9/2007 | Anderson et al. |
| 7,291,104 B2 | 11/2007 | Neisz et al. |
| 7,297,102 B2 | 11/2007 | Smith et al. |
| 7,303,525 B2 | 12/2007 | Watschke et al. |
| 7,326,213 B2 | 2/2008 | Benderev et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,364,541 B2 | 4/2008 | Chu et al. |
| 7,387,634 B2 | 6/2008 | Benderev |
| 7,395,822 B1 * | 7/2008 | Burton et al. .................. 128/885 |
| 7,402,133 B2 | 7/2008 | Chu et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,513,865 B2 | 4/2009 | Bourne et al. |

(56) References Cited

U.S. PATENT DOCUMENTS

| | | |
|---|---|---|
| 7,527,588 B2 | 5/2009 | Zaddem et al. |
| 7,547,316 B2 | 6/2009 | Priewe et al. |
| 7,588,598 B2 | 9/2009 | Delorme et al. |
| 7,601,118 B2 | 10/2009 | Smith et al. |
| 7,608,067 B2 * | 10/2009 | Bonni .................... 604/323 |
| 7,621,865 B2 | 11/2009 | Gellman et al. |
| 7,637,860 B2 | 12/2009 | MacLean |
| 7,686,759 B2 | 3/2010 | Sater |
| 7,691,050 B2 | 4/2010 | Gellman et al. |
| 7,691,052 B2 | 4/2010 | Gellman et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,762,969 B2 | 7/2010 | Gellman et al. |
| 7,766,926 B2 | 8/2010 | Bosely et al. |
| 7,789,821 B2 | 9/2010 | Browning |
| 7,794,385 B2 | 9/2010 | Rosenblatt |
| 7,828,715 B2 | 11/2010 | Haverfield |
| 2001/0000533 A1 | 4/2001 | Kovac |
| 2001/0023356 A1 | 9/2001 | Raz |
| 2001/0027321 A1 | 10/2001 | Gellman et al. |
| 2001/0041895 A1 | 11/2001 | Beyer et al. |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0035369 A1 | 3/2002 | Beyar et al. |
| 2002/0050277 A1 | 5/2002 | Beyar |
| 2002/0055748 A1 | 5/2002 | Gellman et al. |
| 2002/0058959 A1 | 5/2002 | Gellman et al. |
| 2002/0082619 A1 | 6/2002 | Cabak et al. |
| 2002/0091373 A1 | 7/2002 | Berger |
| 2002/0095064 A1 | 7/2002 | Beyar |
| 2002/0095163 A1 | 7/2002 | Beyar |
| 2002/0095181 A1 | 7/2002 | Beyar |
| 2002/0099260 A1 | 7/2002 | Suslian et al. |
| 2002/0128681 A1 | 9/2002 | Broome et al. |
| 2002/0138025 A1 | 9/2002 | Gellman et al. |
| 2002/0147382 A1 | 10/2002 | Neisz et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023137 A1 | 1/2003 | Gellman et al. |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0039453 A1 | 2/2004 | Anderson et al. |
| 2004/0073235 A1 | 4/2004 | Lund |
| 2004/0193215 A1 | 9/2004 | Harari et al. |
| 2004/0225181 A1 | 11/2004 | Chu et al. |
| 2004/0267088 A1 | 12/2004 | Krammerer |
| 2005/0004576 A1 | 1/2005 | Benderev |
| 2005/0038451 A1 | 2/2005 | Rao et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0260618 A1 | 11/2006 | Hodroff et al. |
| 2006/0281964 A1 * | 12/2006 | Burton et al. .................... 600/29 |
| 2006/0287571 A1 | 12/2006 | Gozzi |
| 2007/0015953 A1 | 1/2007 | MacLean |
| 2007/0078295 A1 | 4/2007 | Landgrebe |
| 2007/0173864 A1 | 7/2007 | Chu |
| 2008/0039678 A1 | 2/2008 | Montpetit et al. |
| 2008/0167518 A1 * | 7/2008 | Burton et al. .................... 600/31 |
| 2009/0005634 A1 | 1/2009 | Rane |
| 2009/0012353 A1 | 1/2009 | Beyer |
| 2009/0221867 A1 | 9/2009 | Ogdahl et al. |
| 2009/0221868 A1 | 9/2009 | Evans |
| 2009/0240102 A1 | 9/2009 | Rane et al. |
| 2009/0259092 A1 | 10/2009 | Ogdahl et al. |
| 2010/0010631 A1 | 1/2010 | Otte et al. |
| 2010/0094079 A1 | 4/2010 | Inman |
| 2010/0152528 A1 | 6/2010 | Chapmenan et al. |
| 2010/0168505 A1 | 7/2010 | Inman et al. |
| 2010/0174134 A1 | 7/2010 | Anderson et al. |
| 2010/0261950 A1 | 10/2010 | Lund et al. |
| 2010/0261952 A1 | 10/2010 | Montpetit et al. |

FOREIGN PATENT DOCUMENTS

| | | |
|---|---|---|
| DE | 19544162 | 4/1997 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1342450 B1 | 9/2003 |
| FR | 2787990 A1 | 7/2000 |
| FR | 2852817 | 10/2004 |
| IT | 1299162 | 4/1998 |
| WO | WO9310715 A1 | 6/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937216 A1 | 7/1999 |
| WO | WO9937217 A1 | 7/1999 |
| WO | WO9952450 A1 | 10/1999 |
| WO | WO9953844 A1 | 10/1999 |
| WO | WO9958074 A2 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0030556 A1 | 6/2000 |
| WO | WO0040158 A2 | 7/2000 |
| WO | WO0057796 A1 | 10/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0139670 A1 | 6/2001 |
| WO | WO0145588 A1 | 6/2001 |
| WO | WO0145589 A1 | 6/2001 |
| WO | WO0228312 A1 | 4/2002 |
| WO | WO0228315 A2 | 4/2002 |
| WO | WO0230293 A1 | 4/2002 |
| WO | WO0238079 A2 | 5/2002 |

(56) References Cited

FOREIGN PATENT DOCUMENTS

| | | |
|---|---|---|
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO03013392 A2 | 2/2003 |
| WO | WO03003778 A1 | 4/2003 |
| WO | WO03034939 A1 | 5/2003 |
| WO | WO03067107 A1 | 8/2003 |
| WO | WO03073960 A1 | 9/2003 |
| WO | WO03075792 A1 | 9/2003 |
| WO | WO03086205 A2 | 10/2003 |
| WO | WO03092546 A2 | 11/2003 |
| WO | WO03096928 A1 | 11/2003 |
| WO | WO03096929 A1 | 11/2003 |
| WO | WO2004012626 A1 | 2/2004 |
| WO | WO2004016196 A2 | 2/2004 |
| WO | WO2004017862 A2 | 3/2004 |
| WO | WO2004045457 A1 | 6/2004 |
| WO | WO2005004727 A1 | 1/2005 |
| WO | WO2005037132 A2 | 4/2005 |
| WO | WO2005046511 A2 | 5/2005 |
| WO | WO2005048850 A2 | 6/2005 |
| WO | WO2005079702 A1 | 9/2005 |
| WO | WO2005094741 A1 | 10/2005 |
| WO | WO2005112842 A1 | 12/2005 |
| WO | WO2005122954 A1 | 12/2005 |
| WO | WO2006007190 A1 | 1/2006 |
| WO | WO2006015031 A2 | 2/2006 |
| WO | WO2006031879 A1 | 3/2006 |
| WO | WO2006069078 | 6/2006 |
| WO | WO2006108145 A1 | 10/2006 |
| WO | WO2007002012 A1 | 1/2007 |
| WO | WO2007002071 A1 | 1/2007 |
| WO | WO2007011341 A1 | 1/2007 |
| WO | WO2007014241 A1 | 2/2007 |
| WO | WO2007016083 A1 | 2/2007 |
| WO | WO2007016698 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146742 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |

OTHER PUBLICATIONS

"Access Instrument System with AlloSling Fascia" (5 pages with two pages of Instructions for Use).

"Introducing: AlloSling Fascia the Natural Choice for Suburethral Sling Procedures", Advertisement from UroMed Corporation (1 page).

Advantage A/T™, Surgical Mesh Sling Kit, Boston Scientific, 6 pages (2002).

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).

AlloSource product literature (11pages).

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).

Blaivas, Jerry et al., Pubovaginal Fascial Sling for the Treatment of Complicated Stress Urinary Incontinence, The Journal of Urology, vol. 145, pp. 1214-1218 (Jun. 1991).

Blaivas, Jerry et al., Type III Stress Urinary Incontinence: Importance of Proper Diagnosis and Treatment, Surgical Forum, pp. 473-475, (1984).

Blavis, Jerry, Commentary: Pubovaginal Sling Procedure, Experience with Pubovaginal Slings, pp. 93-101 (1990).

Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).

Capio™ CL—Transvaginal Suture Capturing Device—Transvaginal Suture Fixation to Cooper's Ligament for Sling Procedures, Boston Scientific, Microvasive®, 8 pages, (2002).

Choe, Jong M. et al., Gore-Tex Patch Sling: 7 Years Later, Urology, vol. 54, pp. 641-646 (1999).

Dargent, D. et al., Insertion of a Suburethral Sling Through the Obturator Membrane in the Treatment of Female Urinary Incontinence, Gynecol Obstet Fertil, vol. 30, pp. 576-582 (2002).

Decter, Ross M., Use of the Fascial Sling for Neurogenic Incontinence: Lessons Learned, The Journal of Urology, vol. 150, pp. 683-686 (Aug. 1993).

Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.

Falconer, C. et al., Influence of Different Sling Materials of Connective Tissue Metabolism in Stress Urinary Incontinent Women, International Urogynecology Journal, Supp. 2, pp. S19-S23 (2001).

Gynecare TVT Tension-Free Support for Incontinence, The tension-free solution to female Incontinence, Gynecare Worldwide, 6 pages, (2002).

Handa, Victoria L. et al, Banked Human Fascia Lata for the Suburethral Sling Procedure: A Preliminary Report, Obstetrics & Gynecology, vol. 88 No. 6, 5 pages (Dec. 1996).

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, p.

Intramesh L.I.F.T. Siliconized polyester, Cousin Biotech, 1 page (no date).

Intramesh® L.I.F.T.® Polypropylene Less Invasive Free Tape, Cousin Biotech, 2 pages (no date).

Kersey, J., The Gauze Hammock Sling Operation in the Treatment of Stress Incontintence, British Journal of Obstetrics and Gynaecology, vol. 90, pp. 945-949 (Oct. 1983).

Klutke, John M.D. et al, The promise of tension-free vaginal tape for female SUI, Contemporary Urology, 7 page (Oct. 2000).

Korda, A. et al., Experience With Silastic Slings for Female Urinary Incontience, Aust NZ J. Obstet Gynaecol, vol. 29, pp. 150-154 (May 1989).

Kovac, S. Robert, et al, Pubic Bone Suburethral Stabilization Sling: A Long Term Cure for SUI?, Contemporary OB/GYN, 10 pages (Feb. 1998).

Mitek Brochure, Therapy of Urinary Stess Incontinence in Women Using Mitek GIII Anchors, by Valenzio C. Mascio, MD.

Morgan, J. E., A Sling Operation, Using Marlex Polypropylene Mesh, for the Treatment of Recurrent Stress Incontinence, Am. J. Obst. & Gynecol, pp. 369-377 (Feb. 1970).

Nichols, David H., The Mersilene Mesh Gauze-Hammock for Severe Urinary Stress Incontinence, Obstetrics and Gynecology. vol. 41, pp. 88-93 (Jan. 1973).

Niknejad, Kathleen et al., Autologous and Synthetic Urethral Slings for Female Incontinence, Urol Clin N Am, vol. 29, pp. 597-611 (2002).

Norris, Jeffrey P. et al., Use of Synthetic Material in Sling Surgery: A Minimally Invasive Approach, Journal of Endourology, vol. 10, pp. 227-230 (Jun. 1996).

(56) References Cited

OTHER PUBLICATIONS

O'Donnell, Pat, Combined RAZ Urethal Suspension and McGuire Pubovaginal Sling for Treatment of Complicated Stress Urinary Incontinence, Journal Arkansas Medical Society, vol. 88, pp. 389-392 (Jan. 1992).

Ostergard, Donald R. et al., Urogynecology and Urodynamics Theory and Practice, pp. 569-579 (1996).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).

Readjustable REMEEX® system, Neomedic International, 8 pages (no date).

Ridley, John H., Appraisal of the Goebell-Frangenheim-Stoeckel Sling Procedure, American Journal Obst & Gynec., vol. 95, No. 5, pp. 741-721 (Jul. 1, 1986).

SABRE™ Bioabsorbable Sling, Generation Now, Mentor, 4 pages (May 2002).

SABRE™ Surgical Procedure, Mentor, 6 pages (Aug. 2002).

Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).

Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).

Stamey, Thomas A., M.D., Endoscopic Suspension of the Vesical Neck for Urinary Incontinence in Females, Ann. Surgery, vol. 192 No. 4, pp. 465-471 (Oct. 1980).

Stanton, Stuart L., Suprapubic Approaches for Stress Incontinence in Women, Journal of American Geriatrics Society, vol. 38, No. 3, pp. 348-351 (Mar. 1990).

Stanton, Stuart, Springer-Veglag, Surgery of Female Incontinence, pp. 105-113 (1986).

Studdiford, William E., Transplantation of Abdominal Fascia for the Relief of Urinary Stress Incontinence, American Journal of Obstetrics and Gynecology, pp. 764-775 (1944).

Suport™, Sub-Urethral Perineal Retro-Pubic Tensionless Sling, Matrix Medical (Pty) Ltd, (no date), 1 pg.

T-Sling® (Totally Tension-free) Urinary Incontinence Procedure, Herniamesh, 2 pages (no date).

TVT Tension-free Vaginal Tape, Gynecare, Ethicon, Inc., 6 pages (1999).

Ulmsten, U. et al., An Ambulatory Surgical Procedure Under Local Anesthesia for Treatment of Female Urinary Incontinence, International Urogynecology Journal, vol. 7, pp. 81-86 (May 1996).

Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).

Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).

Vesica® Percutaneous Bladder Neck Stabilization Kit, A New Approach to Bladder Neck Suspenison, Microvasive® Boston Scientific Corporation, 4 pages (1995).

Vesica® Sling Kits, Simplifying Sling Procedures, Microvasive® Boston Scientific Corporation, 4 pages (1998).

Walters, Mark D., Percutaneous Suburethral Slings: State of the Art, Presented at the conference of the American Urogynecologic Society, Chicago, 29 pages (Oct. 2001).

Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).

Horbach, Nicollette, Suburethral Sling Procedures, Genuine Stress Incontinence, Chapter 42, pp. 569-579.

Precision Twist, Low Profile design for Precise Anchor Placement, Boston Scientific Microvasive, 2001 2 pp.

Vesica Sling Kit, Microvasive Boston Scientific, 1997, 6pp.

Precision Tack, The Precise Approach to Transvaginal Sling Procedures, Boston Scientific, 1998, 4pp.

* cited by examiner

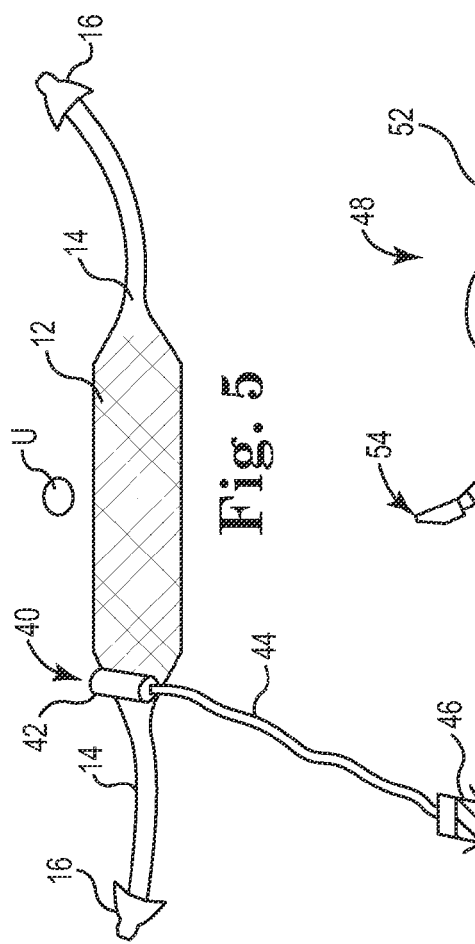
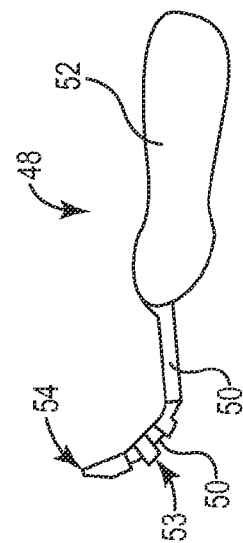
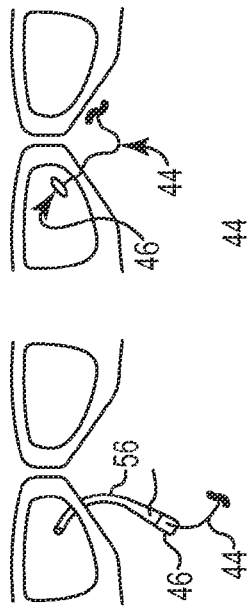
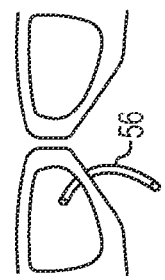
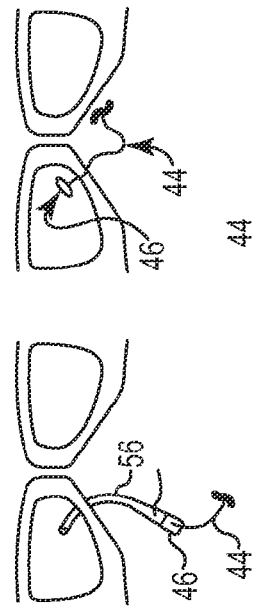
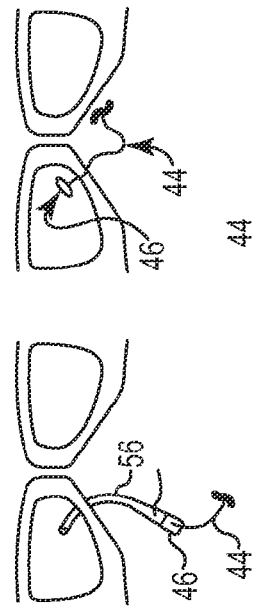

IMPLANT TENSION ADJUSTMENT SYSTEM AND METHOD

PRIORITY

This application claims priority to and the benefit of U.S. Provisional Application No. 61/445,840, filed Feb. 23, 2011, which is incorporated herein by reference in its entirety.

FIELD OF THE INVENTION

The present invention relates generally to surgical methods and apparatus and, more specifically, to a post-implant tension adjustment systems and methods.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

With convention systems and methods, the challenge is with adjusting tension of the sling or implant after the deployment and positioning procedure is complete. It can be difficult to access the implant and increase or decrease tension to improve the patient's outcome.

There is a desire to obtain a minimally invasive yet highly effective system and method of adjusting the urethra or other anatomical pelvic structure or tissue after a mesh implant or like device has been implanted.

SUMMARY OF THE INVENTION

The present invention describes systems and methods of adjusting the urethra or like anatomical structures after implantation of pelvic slings or implants to treat incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness (male and female).

The adjustment system can include two or more small pressure bulbs placed against an endopelvic structure, e.g., the inferior pubic rami, for support. By palpating the bulbs (e.g., bilaterally—one on left and one on right), the pressure can be adjusted without any incisions. The pressure increments, increasing or decreasing, can be relatively minor in order to fine tune the corrective tension of the implant on the urethra. The system can also include one or more check valves and two small reservoirs. At least one of the check valves can be spring loaded on a release side of the system to prevent over-pressurizing of the system.

The implant support portion introduced and deployed beneath the urethra is generally flat to prevent local pressure points on the supported tissue or structure. In addition, this urethra support can be temporarily attached to a manometer to provide feedback on the tension during the procedure. Once the manometer is removed, that port is sealed automatically to prevent leakage.

Various embodiments can include elongate inflation conduits or balloons extending along a portion of the implant, such as the extension portions. As such, inflation or deflation of the conduits or balloons with correspondingly adjust the length or spanning distance of the extension portions to adjust tension of the implant relative to the supported tissue or organ.

Other embodiments can include a fluid or adjustment device provided with the implant, and a conduit extending from the adjustment device to an opposing or distal injection port. An introduction tool and hollow tube assembly can be implemented to deploy the injection port within the patient to provide a port to later facilitate control over the adjustment device to control tension of the implant relative to the supported tissue or organ. The injection port can be anchored to tissue within the pelvic region of the patient.

The various fluid reservoirs, balloons, and inflation and adjustment devices described herein can be included along any portion of the implant 10 to facilitate tension adjustment, including the extension portions and the support portion of the implant. Tension is generally adjusted via displacement of the implant up or down, or by selectively controlling the length or spanning shape of the implant from end to end.

BRIEF DESCRIPTION OF THE DRAWINGS

FIG. 5 depicts an implant having a tension adjustment device, a conduit and an injection port in accordance with embodiments of the present invention.

FIG. 6 depicts an introduction tool in accordance with embodiments of the present invention.

FIGS. 7-10 depict steps of deploying at least the injection port in accordance with the embodiments of FIG. 5.

DETAILED DESCRIPTION OF PREFERRED EMBODIMENTS

Figure 1:
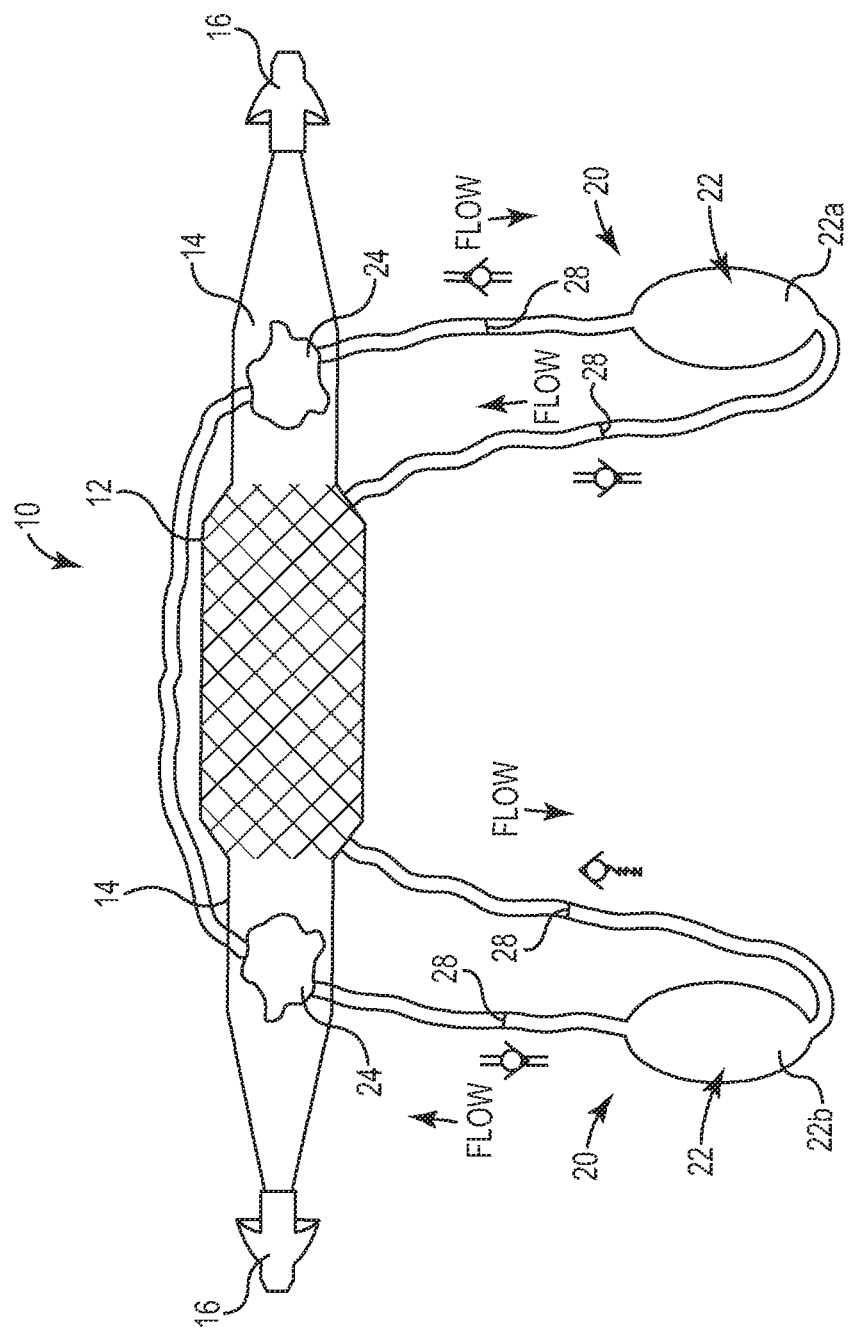
FIG. 1 depicts an implant having a tension adjustment system in accordance with embodiments of the present invention.

Referring generally to FIGS. 1-11, various embodiments of an adjustable implant system 10 and method are provided for use after a sling or implant deployment and positioning procedure, to treat pelvic conditions such as incontinence (male or female) or prolapse. In general, the implants 10 can include a tissue support portion 12, extension portions 14, and a pressure adjustment system or mechanism 20. The implants 10 can further include one or more anchor portions 16. The extension portion 14 can be included to span between or link the support portion 12 and the respective anchoring portions 16. Various portions of the implant 10 can be constructed of polymer materials, e.g., woven, shaped, molded or otherwise formed into or from a generally planar film or sheet material. Examples of acceptable polymer materials available in constructing or forming the implant systems 10 and its components can include polypropylene, polyethylene, fluoropolymers or like biocompatible materials.

Portions of the implant 10, such as the support portion 12, can be formed of a mesh material (woven or non-woven), or formed or patterned by way of a polymer molding process to create a unitary generally homogeneous non-woven, or non-knitted, device or construct. Other embodiments can be formed from an already unitary homogeneous sheet or film via laser cutting, die cutting, stamping and like procedures. Further, various embodiments of the implant 10 can be constructed of opaque, or translucent, polymer materials. The support portion 12 is generally adapted to support tissue, such as that required to treat urinary or fecal incontinence, including the bladder neck, urethra or rectum.

The various implants 10, structures, features and methods detailed herein are envisioned for use with many known implant and repair devices (e.g., for male and female urinary and fecal incontinence solutions), features and methods, including those disclosed in U.S. Pat. Nos. 7,500,945, 7,407,480, 7,351,197, 7,347,812, 7,303,525, 7,070,556, 7,025,063, 6,911,003, 6,802,807, 6,702,827, 6,691,711, 6,652,450, 6,648,921, and 6,612,977, International Patent Publication Nos. WO 2011/072148, WO 2008/057261 and WO 2007/097994, and U.S. Patent Publication Nos. 2011/0124956, 2010/0261955, 2004/0039453, 2002/0151762 and 2002/0147382. Accordingly, the above-identified disclosures are fully incorporated herein by reference in their entirety.

The adjustable implant system 10 can be attached to or otherwise provided with a sling device (such as a mesh incontinence sling) as shown in FIG. 1. The adjustment system 20 can include an inflation system having one or more small pressure bulbs 22 and one or more bladder or reservoir portions 24. Portions of the inflation system, such as the bulbs 22 can be placed against or proximate the inferior pubic rami for support. Various tubes or conduits 26 can be provided to facilitate fluid and operable communication along the system 20 components. The fluid contents of the system 20 can include gas, liquid, gel, and like materials or substances. With such a system 20, tension adjustment can occur days, weeks, month, or even years after implantation of the implant 10. Such a system 20 further permits tension adjustment without requiring invasive external abdominal incisions.

By palpating the bulbs 22 (e.g., bilaterally—a bulb 22a on the right and a bulb 22b on the left), the pressure can be adjusted without any incisions. The pressure increments and decrements can be relatively minor and variable. For instance, the pressure increments can be controlled according to the volumetric and material deformation properties of the bulbs 22, bladders 24 or conduits 26. This can provide fine tuned displacement of a portion of the implant 10 (e.g., extension portions 14) and, in turn, the tension of the implant 10 on the urethra or other anatomical structure or surrounding tissue. The system 10 can also include one or more check valves 28 to provide better control over the intake and release of the fluid pressure. At least one check valve 28 can be spring loaded on a release side of the system to prevent over-pressurizing of the system. In various embodiments, the check valves 28 can be included in the communication with, or within, the conduits 26 or other system 20 components.

FIG. 1 depicts fluid flow and pressure control layouts for embodiments of the present invention. In one embodiment of use, the bilateral configuration of the pressure adjustment system 20 includes use of the bulb 22a and corresponding bladder or reservoir 24 and/or conduits 26 as a pressure increase side, and the bulb 22b and respective components can serve as the pressure release side. Implant tension and positioning adjustment can occur post-procedure. With the system 20 components provided and maintained within the endopelvic space at the time of the implantation procedure, later adjustments can be made through palpation or pressure upon external or internal trigger points or zones, e.g., abdominal, vaginal, perennial, and the like. A physician, or other individuals, can apply pressure or use a finger F to palpate the desired bulb device 22 to control an increase or decrease of pressure in the respective reservoir 24. Tools or other devices can also be utilized to activate or apply pressure to the target bulb device 22 in certain embodiments.

Again, the bulbs 22 can be placed in abuttable contact or positioning with a resistive anatomical structure, such as the pubic bone or like structure. A pressure increase in the pressure adjustment system 20 will generally cause displacement of the implant 10 such that tension is increased on the supported tissue, such as the urethra. A pressure decrease to the pressure adjustment system 20 will generally cause the implant to withdraw a measurable degree to reduce tension on the supported tissue. The correlation between the pressure increase/decrease and the direction of the implant 10 displacement can vary depending on the location of the reservoirs 24 (e.g., top or bottom surface of the implant 10) relative to the supported and surrounding tissue.

Figure 2:
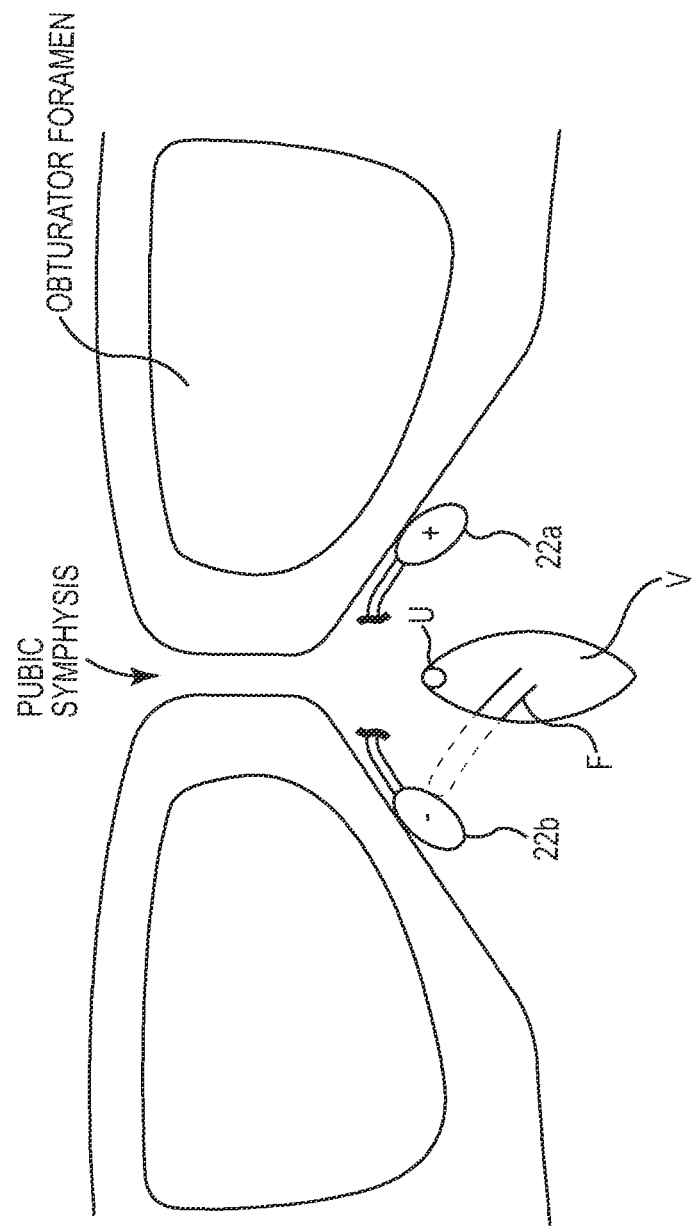
FIG. 2 depicts a schematic view of internal palpation of components of an implant having a tension adjustment system in accordance with embodiments of the present invention.

FIG. 2 depicts an exemplary method of using a finger F inserted within the vaginal opening V to access and activate the respective bulbs 22 against the pubic bone region of the patient to control the pressure (e.g., tension of the implant 10 on the urethra U).

A manometer or other like device can be included (e.g., temporarily) in operable communication with the system 20 to provide feedback on the tension during the tensioning procedure. The manometer can be selectively ported to a portion or component of the system 20 such that the port can be sealed automatically to prevent leakage or a pressure breach after use.

Figure 3:
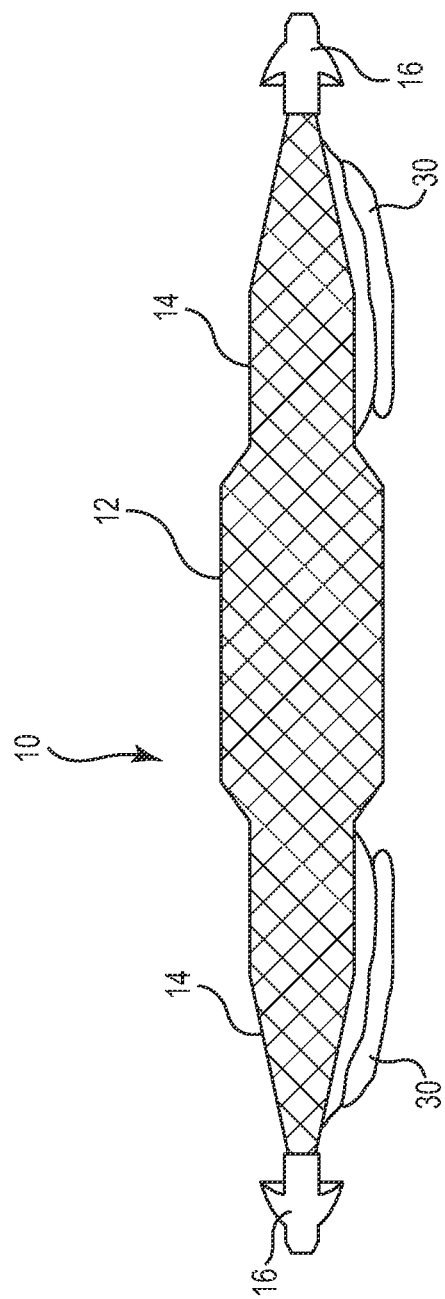
FIG. 3-4 depict an implant having a tension adjustment system, with elongate fluid conduits, in accordance with embodiments of the present invention.
Figure 4:
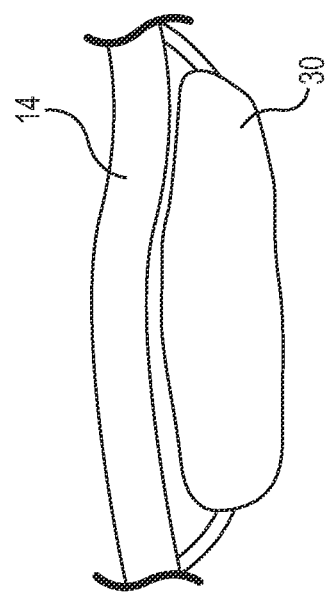

Other embodiments of the present invention are depicted in FIGS. 3-4. In such embodiments, the pressure adjustment system 20 can include one or more elongate balloons or conduits 30. The conduits 30 can be positioned longitudinally along a side or surface of the implant 10 such that fluid or like pressure within the conduits 30 can be selectively controlled (increased or decreased incrementally or variably) to displace a portion of the implant 20 to control tension. In certain embodiments, the conduits 30 are positioned along and adjacent the extension portions 14 of the implant. Again, the support portion 12 is generally adapted to remain flat to avoid pressure points against the supported tissue or anatomical structure. However, in certain embodiments, various channels or conduits can extend within or along the support portion 12 in communication with the other conduits, reservoirs or components of the system 20.

FIG. 4 depicts one of the conduits 30 in an increased pressure state (inflated) to displace the extension portion 14 accordingly to adjust tension. As the conduits 30 are inflated, the conduits 30 expand and shorten to increase tension by shortening the span of length of the respective expansion portion 14. The conduits 30 can be in operable fluid communication with each other to facilitate traversal of the fluid pressure from one side to the other. Alternatively, each conduit 30 (bilateral placement along extension portions 14) can be isolated such that each is subject to separate pressure adjustment. Various tubes and other conduits can be included to facilitate traversal and storage of fluid or like substances or materials such that the conduits 30 can operate as generally elongate reservoirs. Inflation of the conduits 30 can be facilitated with the introduction of a tool or device adapted to introduce liquid, air or like contents in or out of the conduits 30. In one embodiment, the tool can be introduced via a vaginal incision for access to the conduits 30 after the implantation of the implant 10. Other embodiments can include manual palpation as described herein.

The construct of the reservoirs, conduits, tubes, and like components of the adjustment systems 20 can vary greatly depending on the desired application and adjustment needs. For instance, various polymers, metals and like materials can be utilized to construct the components to facilitate the desired flexibility, rigidity, deformation and fluid communication objectives of the particular pressure adjustment embodiments.

Referring generally to FIGS. 5-10, an embodiment of an adjustment system or mechanism 40 is shown. The system 40 can include one or more inflation or adjustment devices 42, one or more conduits or tubes 44 and an injection port 46. The injection port 46 and conduit 44 are in operable fluid communication with the adjustment device 42. In various embodiments, a separate device 42, conduit 44 and port 46 can be included on each extension portion 14 side of the implant 10.

A tool or other device can dock with the implanted injection port 46 to control fluid, pressure or other selective displacement of the adjustment device 42 to control tension of the implant 10 relative to the supported tissue (e.g., urethra). The injection port 46 can include one or more tines or anchoring features to facilitate tissue anchoring of the port 46 within the pelvic region such that the port 46 is accessible (e.g., via vaginal incision) to later adjust the tension. In certain embodiments, the injection port 46 is anchored to muscles, ligaments or fascia proximate the urethra, such as the obturator foramen, internus, membrane or like anatomical tissue or structures.

An insertion and deployment tool 48 can include a flexible needle portion 50 and a handle portion 52. The needle portion 50 can include a flex portion 53, a distal tip 54 (e.g., sharp or blunt), and an outer sleeve or hollow channel tube 56. The tube 56 includes a lumen therethrough adapted to receive and pass the port 46 through. The tube 56 can be c-shaped, enclosed, or take on a variety of other shapes to facilitate deployment and use to pass the port 46. In certain embodiments, a groove or like slot along the length of the tube 56 will facilitate routing of the conduit 44 as the port 46 is passed through the length of the tube 56.

Upon implantation of the sling or implant 10, including the methods of the above-incorporated references, the exemplary deployment steps shown in FIGS. 7-10 for the injection port 46 and conduit 44 can be performed. First, the needle portion 50 of the tool 48 is inserted through a vaginal incision to obtain endopelvic access. The needle portion 50 can carry the hollow tube 56 such that the tip 54 is directed through to target tissue (FIG. 7), such as the obturator internus membrane. The needle portion 50 can be flexible to facilitate this manipulation. From there, the flexible needle 50 is withdrawn to leave the hollow tube 56 is the desired place and orientation for introduction of the port 46 (FIG. 8). The needle 50 can be withdrawn or disengaged from the hollow tube 56 via manual manipulation or a mechanical actuator in the handle 52. The port 46 is then inserted or deployed through a proximal end of the tube 56 and directed up or along the tube 56 (e.g., via tool 48 or another tool or device) for placement, e.g., anchoring within the target tissue or anatomical structure (FIG. 9). The port 46 includes the extending conduit 44 for communication with the device 42 to control tension. The tube 56 can then be withdrawn to leave the port 46 and extending conduit 44 in place (FIG. 10). Tools, devices and techniques can then be used to dock with the injection port 46 to selectively control expansion, retraction or displacement of the adjustment device 42 to control the tension of the implant 10. For instance, a fluid device can dock with the port 46 to introduce fluid into, or withdrawal fluid from, the device 42. Various embodiments of the process can further include later accessing or docking with the implanted port 46 or conduit 44 readily accessible via a vaginal incision to adjust the tension days, weeks, months or even years after implantation.

The injection 46 and conduit 44 configuration of the adjustment system 40 can also be employed with other embodiments of the present invention to provide the desired post-procedure pressure control (inflation and deflation) system, including the embodiments of FIGS. 1-2 and FIGS. 3-4. Such a pressure and tension adjustment system can serve as an alternative system and technique from finger or manual palpation.

Figure 11:
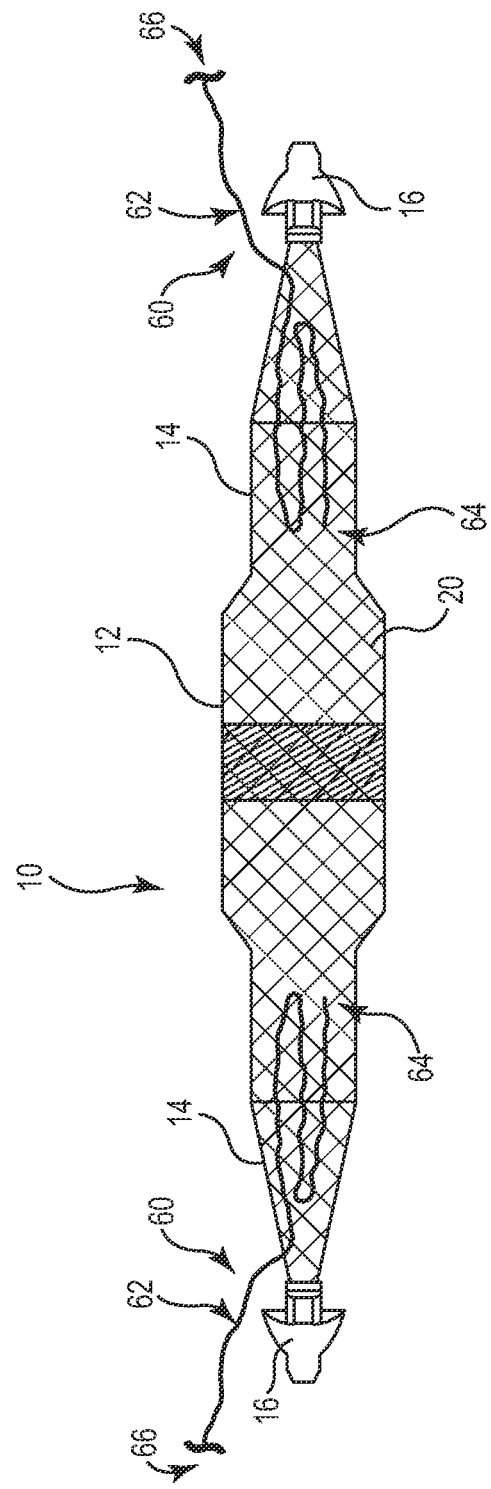
FIG. 11 depicts an implant having a suture pulley tension adjustment system in accordance with embodiments of the present invention.

FIG. 11 shows an embodiment of the system 10 having one or more pulley member or suturing systems 60 having one or more interwoven or looped members or sutures 62 adapted to impose selective elongation and contraction of the implant 10 to provide urethral and sling device adjustment. Various sutures, structures, devices and mechanisms can be employed to achieve the various adjustment devices and components described and depicted herein. A first end 64 of the suture system 60 can be anchored or provided with the implant 10 with a length of the suture 62 looping or traversing a pattern in the implant 10 such that a second end 66 extends out from the implant 10. Pulling on or otherwise extending the second end 66 away from the implant 10 can shorten or buckle a portion of the implant 10, such as the extension portion 14, to increase tension or raise the implant relative to supported tissue. Likewise, releasing the length of the suture 62 back toward the implant 10 can serve to release tension for the implant 10.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. An adjustable pelvic implant system, comprising:
an elongate implant implantable within a pelvic region of a patient, the implant having a support portion, and first and second extension portions each extending laterally from the support portion, with the first extension portion having a first tissue anchor and the second extension portion having a second tissue anchor such that a first extension length is defined from the support portion to the first tissue anchor and a second extension length is defined from the support portion to the second tissue anchor;
a first elongate fluid reservoir provided generally adjacent to and parallel with the first extension portion of the implant to selectively expand and increase tension by shortening a span of the first extension portion; and a second elongate fluid reservoir provided generally adjacent to and parallel with the second extension portion of the implant to selectively expand and increase tension by shortening a span of the second extension portion.

2. The implant system of claim 1, further including a first flexible conduit in communication with the first elongate fluid reservoir.

3. The implant system of claim 1, further including a second flexible conduit in communication with the second elongate fluid reservoir.

4. The implant system of claim 1, wherein the first tissue anchor includes extending tines.

5. The implant system of claim 1, wherein the second tissue anchor includes extending tines.

6. The implant system of claim 1, wherein the support portion is adapted to support a urethra.

7. The implant system of claim 1, wherein the implant is an elongate porous mesh sling adapted to support a urethra to treat urinary incontinence.

8. An adjustable urethral sling system, comprising:
- an elongate mesh sling including a support portion, and first and second extension portions each longer than and extending laterally from the support portion, the first and second extension portions each having distal tissue anchors, and a first extension length is defined from the support portion to the distal tissue anchor of the first extension portion and a second extension length is defined from the support portion to the distal tissue anchor of the second extension portion;
- a tension adjustment mechanism having;
- a first elongate inflatable fluid device provided generally parallel to and in longitudinal alignment with the first extension portion to selectively expand and thereby increase tension by shortening a length of the first extension portion; and
- a second elongate inflatable fluid device provided generally parallel to and in longitudinal alignment with the second extension portion to selectively expand and thereby increase tension by shortening a length of the second extension portion.

9. The sling system of claim 8, wherein the distal tissue anchor of the first extension portion includes extending tines.

10. The sling system of claim 8, wherein the distal tissue anchor of the second extension portion includes extending tines.

11. The sling system of claim 8, wherein at least the support portion is construction of a porous mesh material.

12. The sling of claim 8, wherein the first and second extension portions are constructed of a porous mesh material.

13. The sling of claim 8, wherein the support portion is maintained in a generally flat orientation when the first elongate inflatable fluid device selectively shortens the length of the first extension portion.

14. The sling of claim 8, wherein the support portion is maintained in a generally flat orientation when the second elongate inflatable fluid device selectively shortens the length of the second extension portion.

15. The sling of claim 8, wherein at least the first extension portion includes a tapering portion and the first elongate inflatable fluid device extends adjacent and generally along the path of the tapering portion.

* * * * *